United States Patent [19]

Schwartz

[11] Patent Number: 4,886,741
[45] Date of Patent: Dec. 12, 1989

[54] USE OF VOLUME EXCLUSION AGENTS FOR THE ENHANCEMENT OF IN SITU HYBRIDIZATION

[75] Inventor: Dennis E. Schwartz, Redmond, Wash.

[73] Assignee: Microprobe Corporation, Bothel, Wash.

[21] Appl. No.: 130,709

[22] Filed: Dec. 9, 1987

[51] Int. Cl.$^4$ .................. C12Q 1/70; C12Q 1/68; G01N 33/53; G01N 33/566
[52] U.S. Cl. .................................. 435/5; 435/6; 435/7; 435/21; 435/810; 436/501; 536/26; 536/27; 536/28; 935/77; 935/78
[58] Field of Search .................. 435/5, 6, 7, 21, 810; 436/501; 935/77, 78; 536/26-28

[56] References Cited

FOREIGN PATENT DOCUMENTS 0098373 1/1984 European Pat. Off. .
8605816 10/1986 World Int. Prop. O. .

OTHER PUBLICATIONS

Wood, W. et al., PNAS, 82: 1585-1588 (1985).
Conner, B., et al., PNAS, 80: 278-282 (1983).
Szabo, P. et al., J. Mol. Biol., 115: 539-563 (1977).

Primary Examiner—Robert J. Warden
Assistant Examiner—Jack Spiegel
Attorney, Agent, or Firm—Townsend and Townsend

[57] ABSTRACT

This invention relates to methods for using volume exclusion agents to enhance in situ hybridization rates between short oligonucleotide probes and their target polynucleotides where the cells containing the target polynucleotides are adhered onto a glass substrate. In one aspect, the invention specifically relates to the use of volume exclusion agents to facilitate assay and diagnostic procedures for the detection of a virus, such as human papillomavirus (HPV). In addition, diagnostic kits embracing the above methods are described herein.

12 Claims, No Drawings

USE OF VOLUME EXCLUSION AGENTS FOR THE ENHANCEMENT OF IN SITU HYBRIDIZATION

BACKGROUND OF THE INVENTION

1. Field of the Invention

This invention relates to methods for using volume exclusion agents to enhance in situ hybridization rates between short oligonucleotide probes and their target polynucleotides where the cells containing the target polynucleotides are adhered onto a glass substrate. In one aspect, the invention specifically relates to the use of volume exclusion agents to facilitate assay and diagnostic procedures for the detection of a virus, such as human papillomavirus (HPV). In addition, diagnostic kits embracing the above methods are described herein.

2. Information Disclosure

In situ hybridization is a method of locating or detecting target polynucleotides within intact cells using labeled polynucleotide probes. Typically, the probes have sufficient sequence complementarity to bind to the target under preselected hybridization conditions. The presence and amount of bound probes is determined in accord with the type of label attached to the probes.

Much of the research related to hybridization between target and probe polynucleotides for assay and diagnostic purposes has been directed toward optimizing rates of hybridization. In situ hybridization is particularly problematic due to the inability of the probes to readily enter into the nucleus or cytoplasm in which their target polynucleotides are located. To solve this problem, researchers have attempted, inter alia, to reduce the size of the probe and to alter cell fixation procedures to facilitate entry of the probe into the cytoplasm or nucleus, see generally Singer, R. H., et al., "Optimization of In Situ Hybridization Using Isotopic and Non-Isotopic Detection Methods," Biotechniques 4(3):230–250, 1986, and Haase, A., et al., "Detection of Viral Nucleic Acids by In Situ Hybridization," Methods in Virology, Vol. VII, pp. 189–226, (1984).

U.S. Pat. No. 4,302,204 has disclosed that the presence of volume exclusion agents may increase hybridization rates. This effect has been reported to be due to the exclusion of the probe molecules from the volume occupied by the volume exclusion agent, which allegedly results in an effective increase in probe concentration. Amasino, R. M., "Acceleration of Nucleic Acid Rate by Polyethylene Glycol," Anal. Biochem., 152:304–307 (1986). It has been reported that the effect of dextran sulfate, the most commonly used exclusion agent, was most pronounced in mixed phase hybridizations where the probes exceeded 250 nucleotides. Further, it has been reported that as the probe size decreases, so would the enhancing effect of dextran sulfate on the rate of hybridization, with no effect observed for oligonucleotides of 14 bases. Meinkoth J. and Wahl J., "Hybridization of Nucleic Acids Immobilized on Solid Supports" (Review), Anal. Biochem., 138:267–284 at 268 (1984). The use of volume exclusion to enhance in situ hybridization has also been reported. It was reported that an average length of 400 nucleotides is optimal for hybridization in situ in the presence of dextran sulfate. Hasse, A., supra. at 205.

U.S. Pat. No. 4,689,294 discloses the use of polyacrylate salts and polymethylacrylate salts to enhance the rate of hybridization between two complementary polynucleotide segments. U.S. Pat. No. 4,689,294 is incorporated herein by reference.

The in situ localization of HPV DNA using long biotinylated probes in the presence of dextran sulfate has also been reported by Beckmann, P. M., et al.; "Detection and Localization of Human Papillomavirus DNA in Human Genital Condylomas by In Situ Hybridization with Biotinylated Probes," J. Med. Virol., 16:265–273 (1985); Milde K., Loning, T., "Detection of Papillomavirus DNA in Oral Papillomas and Carcinomas: Application of In Situ Hybridization with Biotinylated HPV 16 probes," J. Oral Pathol., 15:292–296 (1986); and McDougall, J. K., et al., "Methods for Diagnosing Papillomavirus Infection," in Papillomaviruses, Wiley, Chicester (CIBA Foundation Symposium 120), pp. 86–103 (1986).

In the field of nucleic acid hybridization, the need for rapid assay tests for the accurate and reproducible detection of nucleic acids has been a long standing problem. Any procedures that demonstrate a tendency to accelerate the typically multi-hour long processes are of value, especially for hybridization assays to be conducted by clinical laboratories.

A U.S. patent application was filed on Oct. 2, 1987, entitled "Human Papillomavirus Type Diagnosis With Nucelotide Probes, Ser. No. 103,979, and is incorporated herein by reference.

SUMMARY OF THE INVENTION

This invention relates to the discovery that volume exclusion agents are useful for producing dramatic increases in the in situ hybridization rates between short probes and target polynucleotides, particularly where the target nucleotides are within cells adhered to an inert transparent, solid support.

Methods for using volume exclusion agents to enhance in situ hybridization rates between short polynucleotide probes and their complementary target polynucleotides are specifically provided herein. Various volume exclusion agents are described, as well as reaction conditions and reactants for conducting in situ hybridization.

More specifically there is disclosed herein a method for the in situ detection of polynucleotide targets in cells, comprising:

(a) fixing the cells to an inert, transparent, and solid support; and (b) contacting the fixed cells with a hybridization mixture comprising a labeled short probe of about 15 to 50 nucleotides having a nucleotide sequence capable of hybridizing to the target nucleic acids and a volume exclusion agent at a concentration of 2% to 25% (w/v) of the reaction mixture.

A specific system for using the above method to detect HPV is also provided. In addition, this invention embodies the above method in a multi-component kit with a specific description of an in situ hybridization kit for the detection of HPV.

DETAILED DESCRIPTION

This invention relates to the use of volume exclusion agents to facilitate in situ hybridization rates between short polynucleotide probes and complementary target polynucleotides. The volume excluding agents may be any of a variety of polar water soluble or swellable agents which do not interfere with the assay. These agents include polyethylene glycol (PEG) and anionic polymers of polyacrylate or polymethylacrylate and charged saccharidic polymers, especially those which are anionic saccharidic polymers, such as dextran sulfate, which is most preferred. Polyethylene glycol having a MW of between $6-7.5 \times 10^3$ daltons can be used in concentrations (W/V) of between 5–20%. Higher concentrations of PEG can result in undesired precipitation. Those volume exclusion agents in their anionic forms are available in various salt forms, such as sodium, ammonium, or potassium. It is therefore important to select salts that are compatible with the hybridization reactants. For example, the use of a potassium salt form of a volume exclusion agent where a dodecylsulfate surfacant is to be present could lead to unwanted precipitation. The preferred polymer weight is at least 10,000 daltons, and no more than 2,000,000 daltons, with preferred weights being between 100,000 to 1,000,000, especially for the polyacrylate and polymethylacrylate polymers. The most preferred weight for the polymers is between 400,000 to 600,000 daltons. The amount of agent is from 2 to 25 weight percent of the hybridization buffer, but is preferably at least 5 to 20 weight percent, with 8 to 15 weight percent being most preferred.

Volume exclusion agents useful in this invention are commercially available from different sources. Dextran sulfate, sodium salt is available from Sigma Chemical Co., St. Louis, Missouri. Poly(methacrylic acid) (undefined molecular weight) is available from Polysciences, Warrington, Pennsylvania, as a 40% solution neutralized with 5 N sodium hydroxide. Poly(acrylic)acid (at about 90,000, 300,000, and 450,000 molecular weight) is available from Polysciences as a 10% solution neutralized with 10 N sodium hydroxide.

The invention herein is directed toward improving rates of in situ hybridization using the above-described volume exclusion agents. In addition to increasing the rates of in situ hybridization, sensitivity of the assays is also increased. This is reflected in the discovery that, in comparison studies at low concentrations of labeled short probes and target, the presence of an anionic volume excluding agent will permit detection of hybridization where the same assay would not exhibit detectable hybridization in the absence of a volume exclusion agent within a reasonable time frame.

Traditional and accepted in situ hybridization methodologies remain unchanged except for the addition of these agents. The following two review articles provide an overview of the art of in situ hybridization: Singer, R. H., et al., Biotechniques, 4(3):230–250 (1986), and Haase, A., et al., Methods in Virology, Vol. VII, pp. 189–226 (1984), and are incorporated by reference herein.

SAMPLE COLLECTION AND CELL PREPARATION

Clinical samples of cells and tissue can be obtained by standard techniques, such as by scraping, lavage, or biopsy. Typically, samples are collected and fixed to a glass surface. Fixing agents may be precipitants, such as picric and mecuric acid, ethanol, ethanol/acetic acid, methanol and methanol-acetone mixtures, or cross-linking agents, such as formaldehyde, glutaraldehyde, paraformaldehyde-lysine/periodate, ethyldimethylaminopropylcarbodiimide, and dimethylsubserimidate. Commonly used fixation solutions are ethanol and Carnoy's B solution.

Whole tissue can be frozen or perfused and embedded with paraffin prior to sectioning. Alternatively, a biopsy or needle aspiration can be smeared across a glass slide to approximate a monocellular layer. Single cells grown in culture can be directly deposited onto an inert support, centrifuged upon the support, or allowed to grow and adhere to the substrate. The support can be any solid, transparent support, such as glass or plastic. Although glass is typically used, polycarbonate plastics could be readily substituted as a support.

Pretreatments to increase probe diffusion may be helpful, and include acid treatment or protease treatment. Where enzyme labeled probes are anticipated, an inhibitor wash, which inhibits endogenous competing enzyme activity, is useful. Inhibitor wash solutions will vary according to the enzyme chosen for labeling (e.g., methanol/acetic acid for horse radish peroxidase). Polynucleotide targets are not limited to viruses and can be: endogenous nonpathologic nucleic acid sequences; mutations of the normal, wild-type population, regardless of whether they are phenotypically expressed; or nucleic acid sequences arising from the presence of a pathogen, such as virus, bacteria, mycoplasma, rickettsia-like agents, or fungi.

POLYNUCLEOTIDE PROBES

Polynucleotide probes are DNA or RNA oligonucleotides of naturally occurring bases or base analogs which have sufficient complementarity with the target polynucleotides so that stable binding occurs between target and probe. The degree of homology required for stable binding varies with the stringency of the hybridization medium and/or wash medium.

The lengths of the probes which are useful for the given invention are at least 15 bases long, but no more than 50 bases long. These are referred to herein as "short probes." Probes comprising greater than 50 bases herein are termed "long probes." Optimal balance between diffusion rate into the cell and hybridization specificity is achieved by using probes having between 15 and 30 bases, which is the preferred size range.

DNA probes may also be chemically synthesized using commercially available methods and equipment. For example, the solid phase phosphoramidite method can be used to produce short probes for this invention. See, generally, Caruthers, et al., Cold Spring Harbour Symp. Quant. Biol., 47:411–418 (1982); Adams, et al., J. Am. Chem. Soc., 105:661 (1983); and Itakura, et al., Ann. Rev. Biochem. 53:323–356 (1984). DNA probes can also be synthesized by reverse transcription of mRNA.

DNA probes may be cloned in bacterial host cells by traditional recombinations into replication vectors, such as pBR322, M13, or into vectors containing promoters, e.g., the SP6 promoter, and purified from the host cell by cell lysis, DNA extraction, treatment by selected restriction enzymes, and further isolation by gel electrophoresis.

RNA probes may be directly isolated from cells using oligo-dT column chromatography.

For this invention, it is preferred to chemically synthesize short DNA probes, for example by using the Model 380B DNA Synthesizer from Applied Biosystems, Foster City, California, and using reagents supplied by the same company.

When synthesizing a probe for a specific target, the choice of sequence will determine the specificity of the test. For example, by comparing DNA sequences from several virus types, one can select a sequence for virus detection that is either type specific or genus specific.

Comparisons of DNA regions and sequences can be achieved using commercially available computer programs.

For the selection of preferred HPV probes, the genomic sequences of 6 HPV-types were compared for regions of specificity and relative variability using the Microgenie Program available from Beckman Instruments, Palo Alto, California. Preferred sequences for DNA probes useful to detect targets originating from various HPV isolates thought to be etiologic agents of cervical cancer are presented in Table 1.

In the alternative, patent application W086/05816 discloses both a genus specific and type specific region for the HPV genome located within the L1 gene encoding the major component of the viral coat.

Probes may be labeled by any one of several methods typically used to detect the presence of hybrid polynucleotides. The most common method of detection is the use of autoradiography with $^3H$, $^{125}I$, $^{35}S$, $^{14}C$, or $^{32}P$ labeled probes or the like. The choice of radioactive isotope depends on research preferences due to ease of synthesis, stability, and half lives of the selected isotopes. Other labels include ligands which bind to labeled antibodies, fluorophores, chemiluminescent agents, enzymes, and antibodies which can serve as specific binding pair members for a labeled ligand. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes by using DNA synthesizers, by nick translation, by tailing radioactive DNA bases to the 3' end of probes, by treating M13 plasmids having specific inserts with the Klenow fragment of DNA polymerase in the presence of radioactive dNTP, by transcribing cDNA from RNA templates using reverse transcriptase in the presence of radioactive dNTP, or, for example, by transcribing RNA from vectors containing an SP6 promoter using the SP6 RNA polymerase in the presence of radioactive rNTP. The probes can be labeled using radioactive nucleotides in which the isotope resides as a part of the base or sugar moieties, or in which the radioactive component is attached to the nucleotide via a terminal hydroxyl group that has been esterified to a radioactive component such as inorganic acids, e.g., $^{32}P$ phosphate or $^{14}C$ organic acids, or esterified to provide a linking group to the label. Alternative base analogs having nucleophilic linking groups, such as primary amino groups, can then be linked to a label.

Non-radioactive probes are usually labeled by indirect means. Generally, a ligand molecule is covalently bound to the probe. The ligand then binds to a anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring antiligand. Alternatively, any haptenic or antigenic compound can be used in combination with an antibody.

Enzymes of interest as labels will primarily be hydrolases, such as phosphatases, esterases or glycosidases, and oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

HYBRIDIZATION CONDITIONS

Various hybridization solutions may be employed, comprising from about 20 to 60% volume, preferably 30%, of a polar organic solvent. A common hybridization solution employs about 30-60% (v/v) formamide, about 0.5 to 1 M sodium chloride, about 0.05 to 0.1 M buffers, such as sodium citrate, Tris-HCl, PIPES, or HEPES, about 0.05 to 0.2% (v/v) detergent, such as sodium dodecylsulfate or Tween 20, or between 20 mM and minor amounts of EDTA, ficoll (about 300-500 kilodaltons), polyvinylpyrrolidone (about 250-500 kdal), and bovine serum albumin. Also included in the typical hybridization solution will be unlabeled carrier nucleic acids from about 0.1 to 5 mg/ml fragmented nucleic acid, DNA, e.g., fragmented calf thymus DNA or salmon sperm DNA, or yeast tRNA or yeast RNA; and optionally from about 0.5 to 2% wt./vol. glycine. Other additives may also be included, such as the volume exclusion agents which are the subject of the invention described herein.

The maximum effect upon hybridization rates is dependent upon the concentration of volume exclusion agent present in the hybridization medium. The relative effect of the concentration of volume exclusion agents is also known to differ in accordance with the particular agent selected. Dextran sulfate is typically used at about 5-10% (w/v) and polyacrylate is typically able to accelerate hybridization rates to the level of 10% dextran at significantly lower concentrations of between 1-3% (w/v). Polymethylacrylate can require up to 20% (w/v) to achieve the same results as 10% dextran. By following the general principles explained in this document and by examining the provided examples, one of skill can readily design simple experiments that would determine the preferred agent and optimum concentrations for any given hybridization assay.

The particular hybridization technique is not essential to the invention. Hybridization techniques are generally described in Nucleic Acid Hybridization a Practical Approach, Ed. Hames, B. D. and Higgins, S. J., IRL Press 1987; Gall and Pardue (1969), Proc. Natl. Acad. Sci., U.S.A., 63:378-383; and John Burnsteil and Jones (1969) Nature, 223:582-587. As improvements are made in hybridization techniques, they can readily be applied.

The amount of labeled probe which is present in the hybridization solution may vary widely, depending upon the nature of the label, the amount of the labeled probe which can reasonably bind to the cellular target nucleic acid, and the stringency of the hybridization medium and/or wash medium. Generally, substantial excesses of probe over stoichiometric amount of the target nucleic acid will be employed to enhance the rate of binding of the probe to the target DNA or RNA.

Various degrees of stringency of hybridization can be employed. As the conditions for hybridization become more severe, there must be a greater degree of complementarity between the probe and the target for duplex formation to occur. The degree of stringency can be controlled by temperature, ionic strength, and the presence of a partially denaturing solvent. The stringency of hybridization is conveniently varied by manipulation of the concentration of formamide within the range of 0% to 50%. Temperatures employed will normally be in the range of about 20° to 80° C., usually 25° to 50° C. For probes of 15–50 nucleotides in 35% formamide, the optimal temperature range can vary from 20° to 30° C. With routine experimentation, one can typically define conditions which permit satisfactory hybridization at room temperature.

In an in situ hybridization the cells are fixed to a solid support, typically a glass slide. If DNA is to be probed, it is denatured by treatment with heat or alkali. After the cells have been contacted with a hybridization solution at a moderate temperature for an adequate period of time, the slide is introduced into a wash solution having predetermined concentrations of sodium chloride, buffers, and detergents. The time period for the wash may vary from five minutes to three hours or more. The hybridization or wash media can be stringent. Typically, it is the wash solution that most often determines the stringency and facilitates dissociation of mismatched duplexes. After washing the hybridization complex at room temperature with a dilute buffered sodium chloride solution, the complex may now be assayed for the presence of duplexes in accordance with the nature of the label.

Where the label is radioactive, the glass support is dried and exposed to X-ray film. In the alternative, and preferred, is the use of a nuclear track emulsion which is coated upon the glass in the dark, allowed to develop, washed, stained, and viewed under a microscope (Haase, et al., Methods of Virology, Vol. VII, pp. 209–210).

Where the label is fluorescent, the sample is detected by first irradiating it with light of a particular wavelength. The sample absorbs this light and then emits light of a different wavelength which is picked up by a detector (Freifelder, D., Physical Biochemistry, W. H. Freeman & Co., 1982, pp. 537–542).

Where the label is a hapten or antigen, the sample can be detected by using antibodies. In these systems, a signal is generated by attaching fluorescent or enzyme molecules to the antibodies; in some cases, the antibody is labeled with a radioactive probe (Tijssen, P., Practice and Theory of Enzyme Immunoassays, Laboratory Techniques in Biochemistry and Molecular Biology, Burdon, R, H., van Knippenberg, P. H., Eds. Elsevier, 1985, pp. 9–20).

An alternative method of detection is enzymatic detection in conjunction with biotin. Although fluorescence is an alternative label, enzymatic labels in combination with avidin or streptavidin, such as peroxidase or alkaline phosphatase, are preferred. Enzymeconjugated avidin or streptavidin can also be used to bind the enzyme to the probe (Haase, et al., supra). The preferred method utilizes enzymes directly conjugated to probes. The preferred enzyme is alkaline phosphatase.

Ultrasonic energy can be used to accelerate hybridization rates. A description of this technique is described in U.S. SN 130,754 entitled The Use of Ultrasound for the Enhancement of Nucleic Acid Hybridization (our reference file 11652-5) filed Dec. 9, 1987 which is incorporated herein by reference.

The following examples are offered by way of illustration and not by limitation:

EXAMPLE 1

A. Solutions and Buffers

SSC buffer is 0.015 M sodium citrate (pH 7.0), 0.15 M NaCl; PBS is 0.01 M sodium phosphate (pH 7.4), 0.13 M NaCl; and Denhardt's solution is 0.02% Ficoll 400, 0.02% polyvinylpyrolidone (MW 360,000), 0.02% bovine serum albumin. Carnoy's B solution is 10% (v/v) acetic acid, 30% (v/v) chloroform, 60% (v/v) ethanol. HRP substrate solution is 0.4 mg/ml aminoethyl carbazole, 0.025% (v/v) hydrogen peroxide, 0.1 M sodium acetate (pH 4.5). All percentages are weight/volume (w/v) unless otherwise indicated.

B. Cell Culture Techniques

Comparison tests, demonstrating the effect of volume exclusion agents upon the relative hybridization rates between probes and target polynucleotides in situ cytohybridization assays, were conducted using CaSki cells. These host cells are publicly available from the American Type Culture Collection Accession ("ATCC") No. CRL 1550. They were originally derived from cervical cancer patients, and contain approximately 700 copies of HPV-16, arranged in head-to-tail arrays at about 6–7 chromosomal sites.

The CaSki cells are maintained according to the subculturing procedures provided by the ATCC. Briefly, the cells are cultured in 90& RPMI medium 1640 (Gibco Lab., Grand Island, New York), 10% fetal calf serum, 50 units/100 ml penicillin, and 50 mcg/100 ml streptomycin. Caski cells were grown directly upon a painted slide having two or more wells. Approximately 10,000 CaSki cells were spotted on the glass slides in 100 $\mu$l of the appropriate culture media, and grown at 37° C. for 12 hours. This method allows for the generation of a large number of slides, each containing about 20,000 cells which are adhered to the glass surface. Prior to in situ hybridization, the slides are dipped twice into PBS solution, fixed in Carnoy's B solution for 3 minutes, and then dipped once in 95% ethanol. The slides were lightly blotted to remove excess solution, air-dried for 10 minutes, and stored at −20° C. until used.

C. Probe DNA

Probe DNAs, which are complementary to the HPV-16 genome and other HPV genomes, can be obtained from the various laboratories which actively conduct research in this general area. The probes are generally available as recombinant inserts of a replication or cloning vector, such as pBR322. HPV-16 probes can also be obtained using CaSki cells as a primary source for the recombinant insert. Methods for obtaining inserts complementary to HPV-16 are as described in Maniatis, T., Fritsch, E.F., and Sambrook, J., 1982, Molecular Cloning: A Laboratory Manual, Cold Spring Harbor Laboratory, Cold Spring Harbor, New York. The specific inserts can be selected from the genomic library using appropriate synthetic probes described in Table 1.

Short probes of less than 50 bases can be synthesized on an Applied Biosystems DNA synthesizer (Model 380B) as previously described. DNA probe purification is accomplished by either fractionation of the tritylated product with a high pressure liquid chromatography system, using a reverse phase column, or by fractionation using a 20% polyacrylamide gel containing 7M urea.

For the detection of HPV, a sequence analysis of the genomic DNA reveals that there are numerous DNA sequences within the viral genomes which will permit generic detection, as well as subtype specific detection. The sequences in Table 1 are merely illustrative of several sequences which will serve to detect HPV, both generically and with subtype specification. A comparison of the different genomes for HPV by one skilled in this art will reveal other sequences that can adequately serve as probes.

Short DNA probes can be prepared with a 5' terminal biotin. Initially, DNA probes are prepared with a 5' terminal aminoethyl group. The probes are synthesized as described by Applied Biosystems (Applied Biosystems, User Bulletin, Issue No. 13, Nov. 9, 1984). After 24 cycles of nucleotide synthesis, an extra cycle is added in which the 5' hydroxyl group of the DNA probe is coupled with an activated aminoethylphosphate triester derivative. Following deblocking, the 5' end of the probe contains a nucleophilic aminoethyl group that can be used for coupling with a variety of ligands.

The probe is biotinylated at the aminoethyl group by treatment with the N-hydroxysuccinimide ester of biotin (Pierce Chemical Co., Rockford, Illinois) (0.01 M, pH 8) at room temperature for 30 minutes. The resulting biotinylated DNA probe is separated from unconjugated biotin by column chromotography using Sephadex G25.

D. Hybridization

Comparison studies of the effect of dextran sulfate can be carried out by following the directions below and running parallel experiments, wherein the hybridization solutions are otherwise identical except for the presence of 10% (w/v) dextran sulfate. Thirty microliters of short probe hybridization solution containing 20 mM PIPES at pH 7.4, 500 mM NaCl, 0.05% (w/v) NaPPi, 35% (v/v) formamide. 1 x Denhardt's solution, 200 µg/ml calf thymus DNA, 200 µg/ml yeast RNA, and 20 ng of $^{32}$P- or biotin-labeled short probe is layered over the cells fixed on the glass sides. A siliconized glass or plastic coverslip is placed over the solution, and the samples are incubated in a humidified chamber for 7 minutes at 90° C., and then in a humidified chamber for 1 hour at 37° C. Following removal of the coverslip by soaking in 2 x SSC, the sample is stringently washed twice (5 min./wash) in 2x SSC at room temperature.

E. Detection of Labeled Probe

Detection of $^{32}$p-labeled probe is accomplished with autoradiography.

Detection of biotin-labeled probe is by a streptavidin conjugate of alkaline phosphatase.

A commercially prepared conjugate of alkaline phosphatase with streptavidin (75 µl) is added to the sample and incubated for 30 minutes at room temperature (Bethesda Research Labs, Gaithersburg, MD). The sample is washed in 2 x SSC for 5 minutes, then in 2 x SSC, 0.1% triton X-100 for 5 minutes. The slide is very lightly blotted on its end to remove excess liquid, and 75 µl NBT solution (0.1 M Tris-HCl at pH 8.5, 50 mM MgCl$_2$, 0.1 M NaCl containing 33 µg/ml nitrobluetetrazolium (NBT) and 25 µl/ml 5-Bromo-4-chloro-3-indolyl phosphate (BCIP)) is added and incubated for 3 hours at room temperature in the dark. The sample is then washed with PBS for one minute and mounted for viewing under a microscope.

F. Results

Comparison results of short probes of HPV-16, hybridizing to CaSki cells in the presence or absence of volume excluders, indicated that volume excluders will significantly accelerate the hybridization rate between probes and target polynucleotides immobilized on glass slides. Using a densitometer to optically read autoradiographic results, it appeared that the use of volume excluders accelerated the rates or extent of hybridization as much as twentyfold. A precise quantative measurement was not possible, due to the absence of a rigorous linear relationship between hybridization rates and optical density.

EXAMPLE 2

A. Tissue Collection

1. Samples for testing the presence of HPV target polynucleotides are obtained from female patients during pelvic examinations. Cervical smears or cell samples from the anogenital region are obtained using acceptable medical practices and are immediately fixed in 95% ethanol. Specifically, a cell smear is placed on a standard glass microscope slide, sprayed with a 95% ethanol fixative, and stored at −20° C.

B. Prehybridization Procedures

Prior to hybridization, the cervical smears are soaked in 95% ETOH for at least two hours at room temperature (or at 4° C., overnight). The slides are then treated as described in Examples 1.

C. Hybridization

Immediately following treatment for endogenous peroxidase activity, the samples are exposed to 100 µl of hybridization reaction mixture, comprising 10 ng of short, biotinylated, probe/100 µl;20 mM PIPES, pH 7.5; 0.5 M NaCl; 50% (v/v) formamide; 10% dextran sulfate; 1 X Denhardt's solution; 0.05% Na pyrophosphate; 200 µg/ml yeast RNA; and 200 µg/ml denatured salmon sperm DNA. The reaction mixture is covered with a glass coverslip, and denaturation is achieved by treating the mixture to 7 minutes at 90° C. The reaction mixture is allowed to hybridize at room temperature for 60 minutes.

Following hybridization, the coverslip is removed in a solution of 2 x SSC/0.1% Tween 20, and the slide washed in the solution for 10 minutes at room temperature. Two hundred µl of commercially prepared streptavidin-alkaline-phosphatase complex (Bethesda Research Labs, Gaithersburg, MD) are added to the sample and the sample is incubated for 30 minutes in a humidified chamber at room temperature. After washing, 200 µl of NBT solution are added to the samples, which are then incubated for 30 minutes at room temperature in the dark. The slides are then washed in PBS/0.1% Tween 20 for 5 minutes at room temperature, and the cell smear is permanently mounted with a cover slip and mounting solution.

EXAMPLE 3

Volume exclusion agents will also enhance the hybridization rate and sensitivity of assays using short probes directly linked to an enzyme.

Direct conjugation of alkaline phosphatase to short probe involves conjugation via heterobifunctional reagents. The synthetic probe is synthesized as described herein with a linker arm reagent attached to the terminal 5'-hydroxyl.

An aminohexyl linker arm with a terminal amino group is attached to the 5'-hydroxyl of the synthetic oligodeoxynucleotide on an automated DNA synthesizer as the last step in the synthesis. The reagent used for linker arm introduction is 6-(methoxytritylamino)-hexyl 2-cyanoethyl N,N-diisopropylphosphoramidite, prepared from 6-aminohexanol in a manner similar to the synthesis of the 3-(methoxytritylamino)propyl methyl N,N-diisopropylphosphoramidite, as described by B. A. Connolly, Nucl. Acids Res., 15:3131 (1987). The linker arm was attached to the probe, and the deprotected probe purified in a method similar to the methods described in the Connolly reference.

Alkaline phosphatase is thiolated with dithiobis(succinimidylpropionate) ("DSP") and the oligonucleotide is derivatized with the thiol-reactive agent N-succinimidyl(4-iodoacetyl)aminobenzoate ("SIAB") through the amino linker arm. SIAB-oligonucleotide is prepared by adding 1.2 mg SIAB to 300 μg of the oligonucleotide, reacting for one hour at room temperature, and then desalting over a G-25 column, in 0.02 M sodium phosphate/5 mm EDTA at pH 6.0/5 mM EDTA.

DSP-AP is prepared by adding 800 μg DSP to 4 mg alkaline phosphatase. The reaction is allowed to proceed for 30 minutes at room temperature, and then is reduced with dithiothreitol for 15 minutes at room temperature and desalted over a G-25 column in 0.02 M sodium phosphate at pH6.0.

The SIAB-oligonucleotide is mixed with the DSP-AP at a 4:1 oligo:AP ratio. 5 M NaCl is added to the reaction to bring the final NaCl concentration to 3 M, and the pH is brought to 7.5 with 0.1 volume 1 M Tris pH 7.5. The reaction is allowed to proceed overnight (16 hours) and then stopped with N-ethymaleimide (2 μl of 10 ng/ml). The conjugate is separated from free oligo by chromatography on a P-100 column and free alkaline phosphatase is removed by DEAE chromatography.

For the in situ assay, CaSki cells are first pretreated with a blocking buffer of 1.0 M ethanolamine pH 8.0, 0.2 M HEPES. 5 x Denhardts, 0.2 mg/ml hydrolyzed yeast RNA, .5% triton x-100. The target is then denatured in 0.2 N NaOH for 1 minute at room temperature.

Following target denaturation, the probe (conjugate) is hybridized to the target. The probe is at a concentration of 50 ng/ml in 5% Dextran sulfate, 0.5% triton X-100, 0.2 M HEPES pH 7.5, 5 X Denhardts, .2 μg/ml hydrolyzed yeast RNA. Following hybridization for 30 minutes at room temperature, the cells are washed twice in 1 M Tris/0.1% Triton-X-100 at room temperature. Signal is then developed in 0.1 M Tris pH8.5, 50 mM MgCl$_2$, 0.1 M NaCl containing 33 μg/ml nitrobluetetrazolium (NBT) and 25 μg/ml BCIP (5-Bromo-4-chloro-3-indolylphosphate).

EXAMPLE 4

A test kit for the detection in situ of HPV in cervical cell smears relies on the methodology described in Example 2. The test kit includes all of the required components for collection processing and evaluation of multiple samples. Part A of the kit contains an Ayer's spatula for sample collection, glass slides, and ethanol as a fixative reagent. Part B contains reagents for processing the slides, including control smears having been prefixed with either positive or negative cells. The reagents include a denaturation reagent of formamide and giemsa for a cytoplasmic counter stain; biotinylated probes to HPV subtypes, 6, 11, 16, 18, 31, 33, and 35; wash solutions in powder, tablet or liquid form; and enzyme substrate tablets in powder or liquid form.

Instructions will be provided in the kit and will follow the methodology described in Example 2.

PREFERRED EMBODIMENT

1. A kit designed for the in situ detection of HPV in cell smears.

2. The kit of embodiment 1 having components comprising instructions, sample collection devices, glass slides, fixative reagents, denaturation reagents, washing reagents, and labeled short probes.

3. The kit of embodiment 2 having (a) probes which are detected by enzymatic reactions, and (b) enzyme substrate reagents which react in a detectable manner to the presence of said probe.

TABLE 1

All probes are 24 nucleotides in length and are complementary to Human Papillomavirus (HPV) mRNA. Listed are the sequences of the probes, the HPV Type detected by the probe, the gene detected by the probe, the coordinates in HPV-6 and HPV-16 to which the probe hybridizes (Coordinate #1 is the first G in the HpaI site on the 5' side of the E6 gene) and the GC content of the probe. The nucleotide coordinates in HPV-18 are taken from J. Gen. Vir., 61 67:1909–1916 (1986).

| Probe Sequence | HPV Type | Gene | Coordinates | GC Content |
|---|---|---|---|---|
| 1. 5'GGTTGAACCGTTTTCGGTCCCTCC 3' | 6/11 | E6 | 29–52 | 14/24 |
| 2. 5'CTGTCACATCCACAGCAACAGGTC 3' | 6/11 | E7 | 694–717 | 13/24 |
| 3. 5'CAGAATAGCCATATCCACTGTCCG 3' | 6/11 | E1 | 1229–1252 | 12/24 |
| 4. 5'GTGGTATCTACCACAGTAACAAAC 3' | 6/11 | E4 | 6763–6786 | 10/24 |
| 5. 5'CTTCAGGACACAGTGGCTTTTGAC 3' | 16 | E6 | 420–444 | 12/24 |
| 6. 5'GAAGCGTAGAGTCACACTTGCAAC 3' | 16 | E7 | 734–758 | 12/24 |
| 7. 5'CAACGCATGTGCTGTCTCTGTTTC 3' | 16 | E1a | 1051–1075 | 12/24 |
| 8. 5'CACTTCCACTACTGTACTGACTGC 3' | 16 | E1b | 1366–1390 | 12/24 |
| 9. 5'GTCTCCATCAAACTGCACTTCCAC 3' | 16 | E2 | 3103–3127 | 12/24 |
| 10. 5'CTGTGCAACAACTTAGTGGTGTGG 3' | 16 | E4 | 3507–3531 | 12/24 |
| 11. 5'CAGACACACAAAAGCACACAAAGC 3' | 16 | E5 | 3901–3925 | 11/24 |
| 12. 5'CAGTACGCCTAGAGGTTAATGCTG 3' | 16 | L2 | 5109–5133 | 12/24 |
| 13. 5'AATGTCTTAATTCTCTAATTCTAG 3' | 18 | E7 | 527–550 | 6/24 |
| 14. 5'GGATTCAACGGTTTCTGGCACCGC 3' | 18 | E7 | 627–650 | 14/24 |
| 15. 5'CCTGTCGTGCTCGGTTGCAGCACG 3' | 18 | E7 | 728–751 | 16/24 |
| 16. 5'ATTTTGGGGCTCTAAATGCAATAC 3' | 18 | E7 | 828–851 | 9/24 |
| 17. 5'CTAGAATTAGAGAATTAAGACATT 3' | 18 | E6 | 321–344 | 6/24 |
| 18. 5'GCGGTGCCAGAAACCGTTGAATCC 3' | 18 | E6 | 422–445 | 14/24 |
| 19. 5'TCGTCGGGCTGGTAAATGTTGATG 3' | 18 | E7 | 725–748 | 12/24 |
| 20. 5'GAATGCTCGAAGGTCGTCTGCTGAG 3' | 18 | E7 | 823–847 | 11/25 |
| 21. 5'GAGTTACAGGACTAAAGGGTGTTC 3' | | | | 12/24 |

We claim:

1. A method for the in situ detection of polynucleotide targets in cells, comprising:
    (a) fixing the cells to an inert, transparent, and solid support;
    (b) contacting the fixed cells with a hybridization mixture comprising labeled short probes or between 15 and 30 nucleotides having a nucleotide sequence capable of hybridizing to the polynucleotide targets and a volume exclusion agent at a concentration of 2% to 25% (w/v) of the hybridization mixture;

(c) washing excess short probes from the solid support, wherein steps (b) and (c) are completed in 4 hours or less; and (d) detecting labeled probes hybridized to said cells, wherein said detecting of probe is correlated to detection of said polynucleotide targets.

2. The method of claim 1 wherein the volume exclusion agent is polyethylene glycol or an anionic polymer selected from the group consisting of polyacrylate, polymethylacrylate, and polysaccharidic polymers.

3. The method of claim 2 wherein the polysaccharidic polymer is dextran sulfate in a concentration of 5% to 20%.

4. A method of claim 1 wherein the labeled probe will bind to target polynucleotides arising from infection of the cells by a type of human papilloma virus.

5. The method of claim 4 in which the probes are biotinylated.

6. The method of claim 4 in which the probes are directly conjugated to an enzyme.

7. The method of claim 6 in which the enzyme is alkaline phosphatase.

8. The method of claim 4 wherein the human papilloma virus isolates are from cells originating from the cervix or tissue of the anogenital region.

9. The method of claim 1 wherein the support is glass.

10. A kit for the in situ detection of polynucleotide targets in cells by nucleic acid hybridization methodology comprising hybridization and washing steps wherein the hybridization and washing steps are completed in four hours or less, said kit comprising:

(a) fixation reagents for the fixation of cells to an inert support;

(b) hybridization reagents for assaying the fixed cells, comprising an in situ hybridization reaction mixture which comprises labeled short probes of between 15 and 30 nucleotides and a volume exclusion agent at a concentration of 2 to 25% of the reaction mixture, wherein said reaction mixture effects detectable hybridization of said probe to the polynucleotide target in said fixed cells in a hybridization period of about 1 hour.

11. The kit of claim 10 wherein the volume exclusion agent is an anionic polymer selected from the group consisting of polyacrylate, polymethylacrylate, and polysaccharidic polymers.

12. The kit of claim 11 wherein the polysaccharidic polymer is dextran sulfate in a concentration of 5% to 20%.

* * * * *